(12) United States Patent
Biggs

(10) Patent No.: US 9,430,921 B2
(45) Date of Patent: Aug. 30, 2016

(54) SYSTEMS AND METHODS FOR GENERATING DAMPED ELECTROMAGNETICALLY ACTUATED PLANAR MOTION FOR AUDIO-FREQUENCY VIBRATIONS

(71) Applicant: Taction Technology Inc., Los Gatos, CA (US)

(72) Inventor: Silmon James Biggs, Los Gatos, CA (US)

(73) Assignee: TACTION TECHNOLOGY INC., Los Gatos, CA (US)

( * ) Notice: Subject to any disclaimer, the term of this patent is extended or adjusted under 35 U.S.C. 154(b) by 0 days.

(21) Appl. No.: 14/864,278

(22) Filed: Sep. 24, 2015

(65) Prior Publication Data

US 2016/0086458 A1    Mar. 24, 2016

Related U.S. Application Data

(60) Provisional application No. 62/054,712, filed on Sep. 24, 2014, provisional application No. 62/101,985, filed on Jan. 10, 2015.

(51) Int. Cl.
| | | |
|---|---|---|
| *H04R 1/00* | (2006.01) | |
| *G08B 6/00* | (2006.01) | |
| *H04R 1/10* | (2006.01) | |
| *F16F 7/10* | (2006.01) | |

(Continued)

(52) U.S. Cl.
CPC .............. *G08B 6/00* (2013.01); *A61H 23/00* (2013.01); *F16F 7/1011* (2013.01); *F16F 15/03* (2013.01); *H04R 1/1091* (2013.01); *H04R 2460/13* (2013.01)

(58) Field of Classification Search
CPC ...... F16F 7/1011; F16F 15/03; A61H 23/00; H04R 1/1091; H04R 2460/13
USPC .............................................. 381/151; 600/25
See application file for complete search history.

(56) References Cited

U.S. PATENT DOCUMENTS

| 6,603,863 | B1 | 8/2003 | Nagayoshi | |
|---|---|---|---|---|
| 8,767,996 | B1* | 7/2014 | Lin ...................... | H04R 1/1091 381/370 |
| 2003/0015929 | A1* | 1/2003 | Lee ........................ | H02K 5/24 310/81 |

(Continued)

FOREIGN PATENT DOCUMENTS

WO    WO2013134388 A1    9/2013

OTHER PUBLICATIONS

International Search Report Application No. PCT/2015/51888, International Filing Date Sep. 24, 2015, Mailing Date Feb. 2, 2016.

*Primary Examiner* — Ahmad F. Matar
*Assistant Examiner* — Katherine Faley
(74) *Attorney, Agent, or Firm* — Kramer Levin Naftalis & Frankel LLP

(57) ABSTRACT

A vibration module for applying vibrational tractions to a wearer's skin is presented. Use of the vibration module in headphones is illustrated for providing tactile sensations of low frequency for music, for massage, and for electrical recording and stimulation of the wearer. Damped, planar, electromagnetically-actuated vibration modules of the moving magnet type are presented in theory and reduced to practice, and shown to provide a substantially uniform frequency response over the range 40-200 Hz with a minimum of unwanted audio.

42 Claims, 14 Drawing Sheets

(51) Int. Cl.
*F16F 15/03* (2006.01)
*A61H 23/00* (2006.01)

(56) References Cited

U.S. PATENT DOCUMENTS

| | | |
|---|---|---|
| 2006/0045298 A1* | 3/2006 | Westerkull ............. H02K 33/18 381/326 |
| 2006/0293722 A1 | 12/2006 | Slatkine et al. |
| 2007/0290988 A1 | 12/2007 | Nogami et al. |
| 2008/0194962 A1 | 8/2008 | Randall |
| 2010/0134225 A1 | 6/2010 | Yajima et al. |
| 2010/0316235 A1* | 12/2010 | Park ....................... H04R 1/025 381/151 |
| 2012/0025742 A1 | 2/2012 | Masahiko |
| 2012/0027222 A1* | 2/2012 | Kirsch ................ B60R 11/0217 381/86 |
| 2013/0022220 A1* | 1/2013 | Dong ..................... H04R 5/023 381/151 |
| 2013/0204169 A1* | 8/2013 | Poepperling ....... A61H 23/0263 601/46 |
| 2013/0225915 A1* | 8/2013 | Redfield .............. A61N 5/0618 600/28 |

* cited by examiner

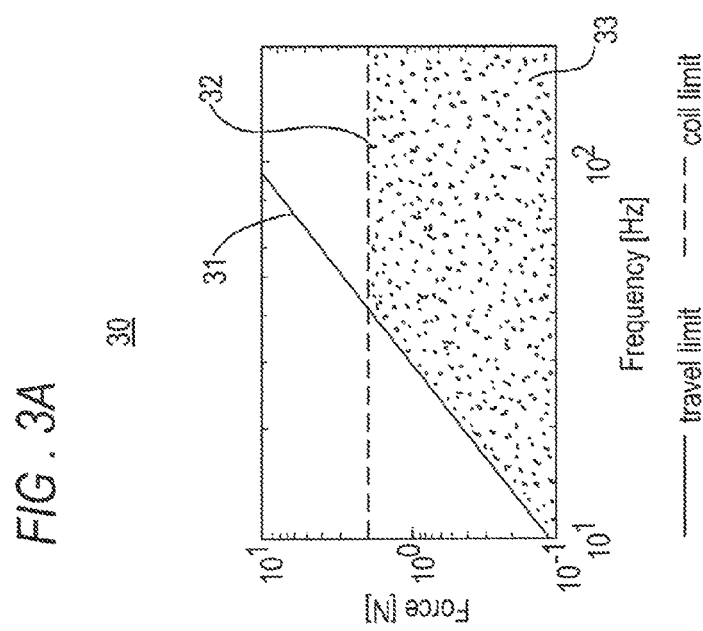
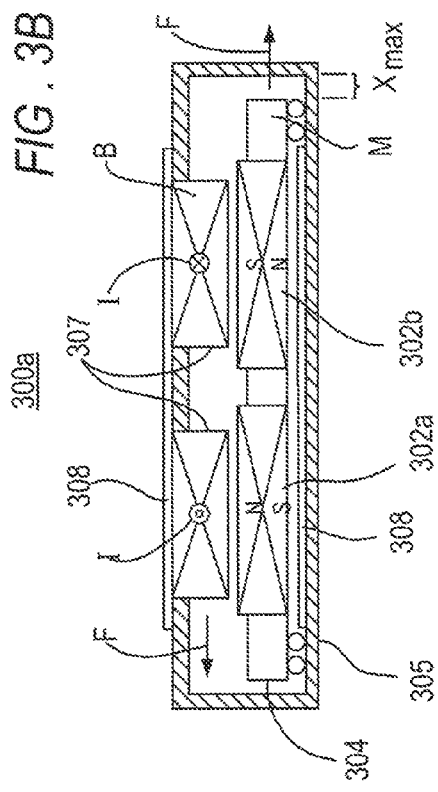
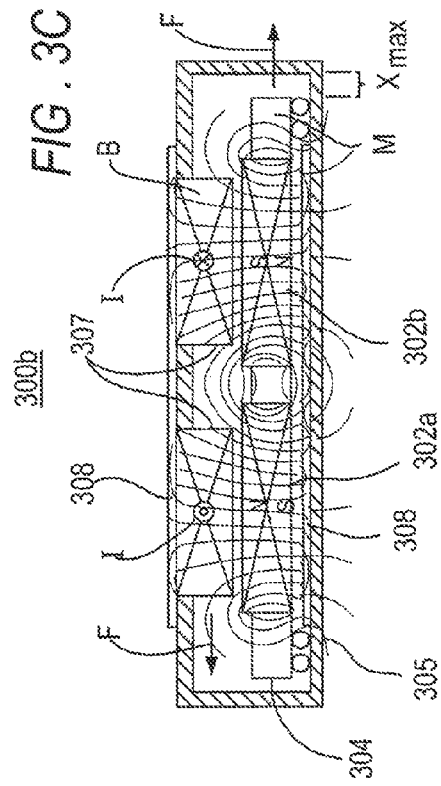
FIG. 3A
FIG. 3B
FIG. 3C

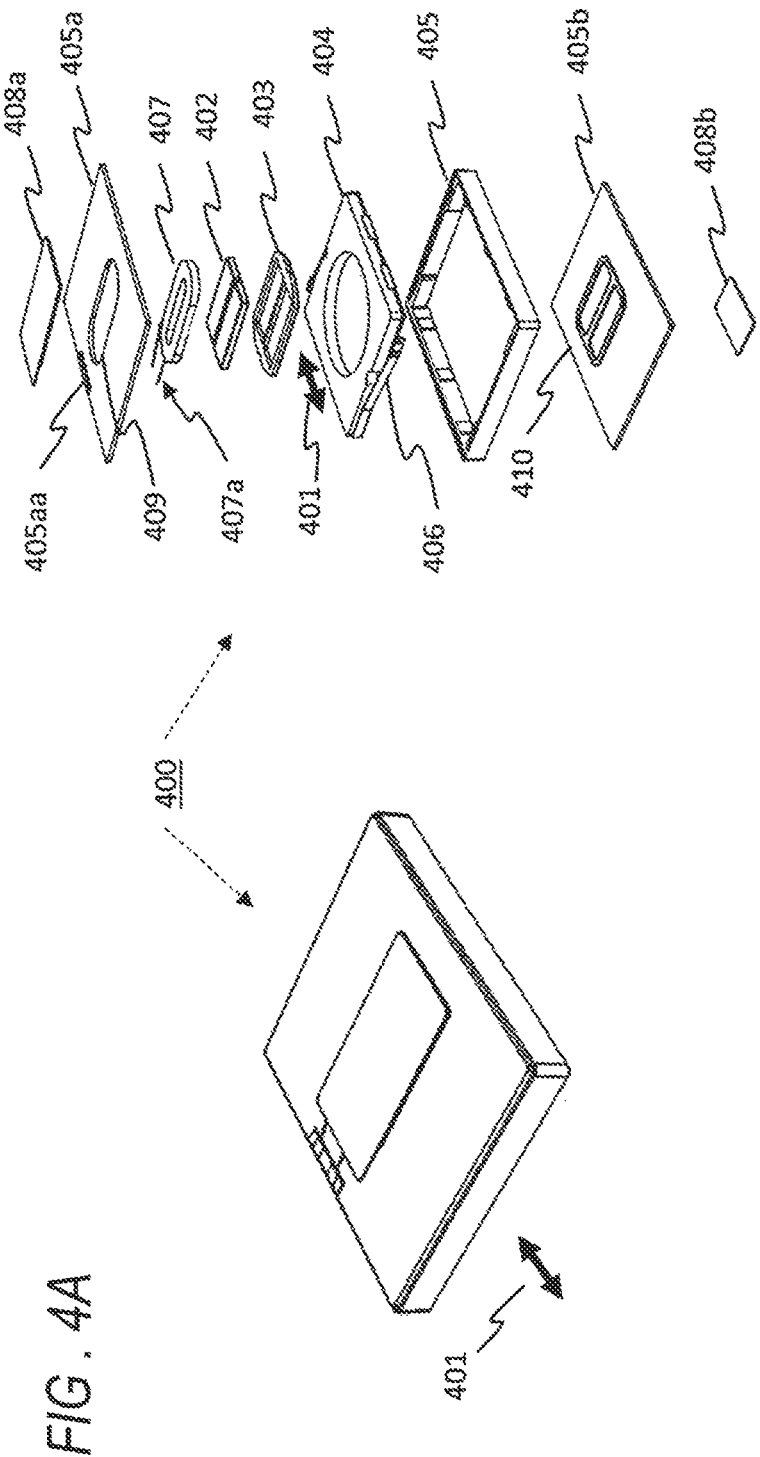

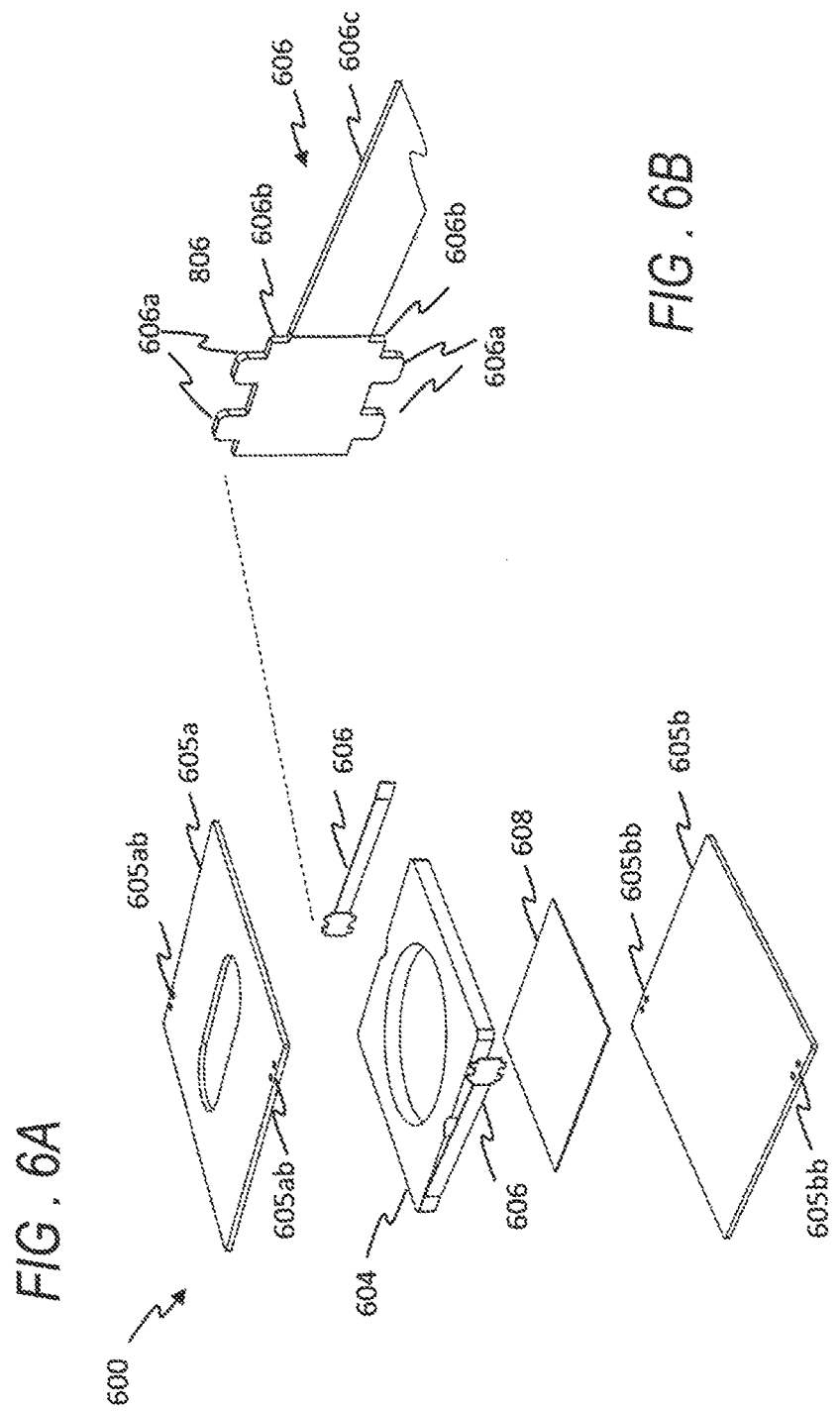

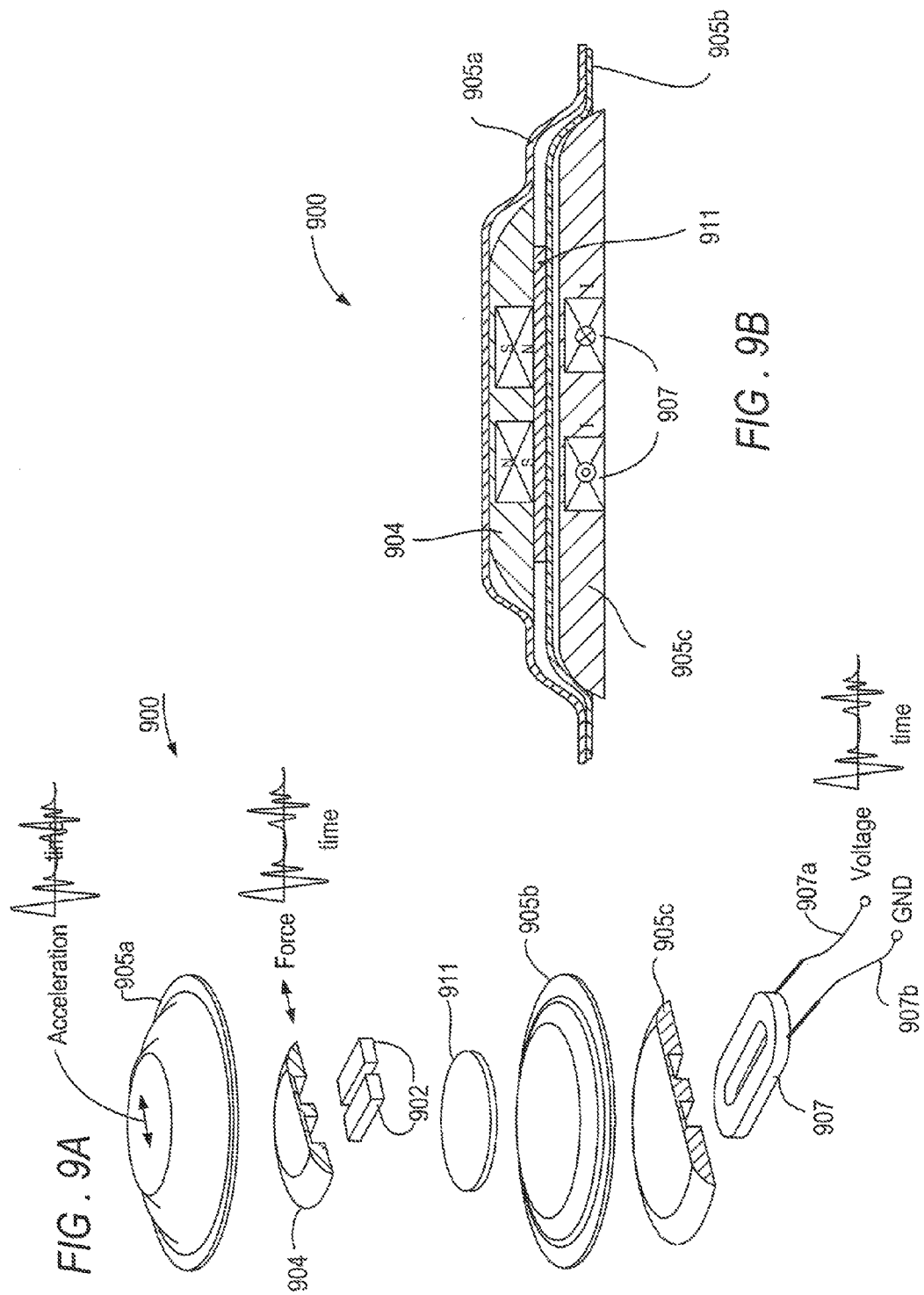

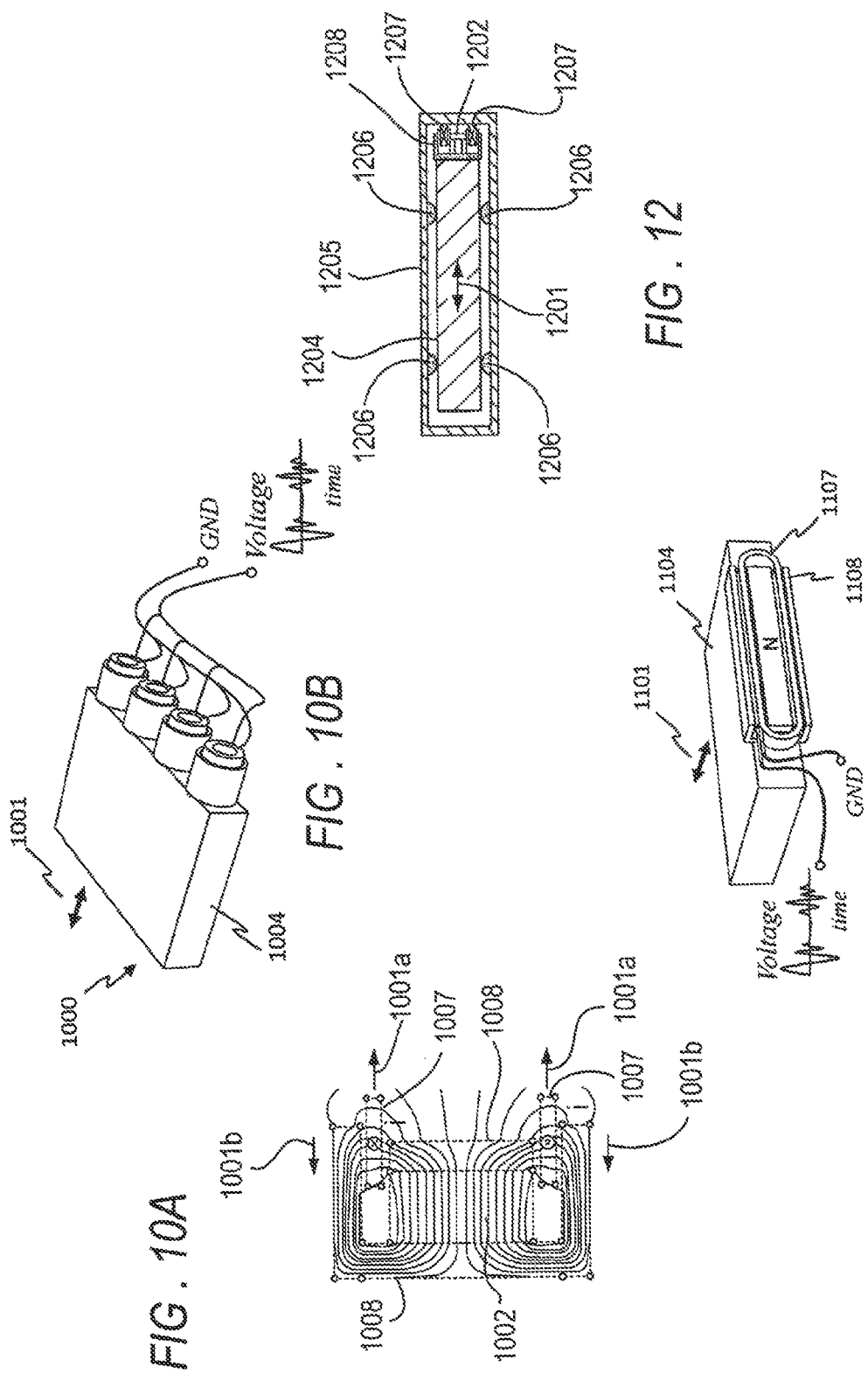

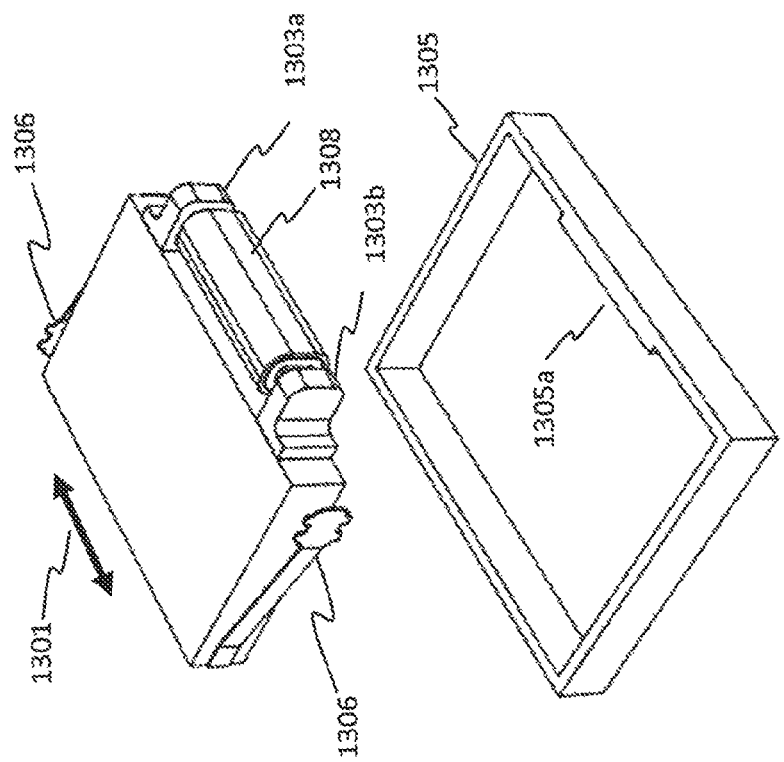
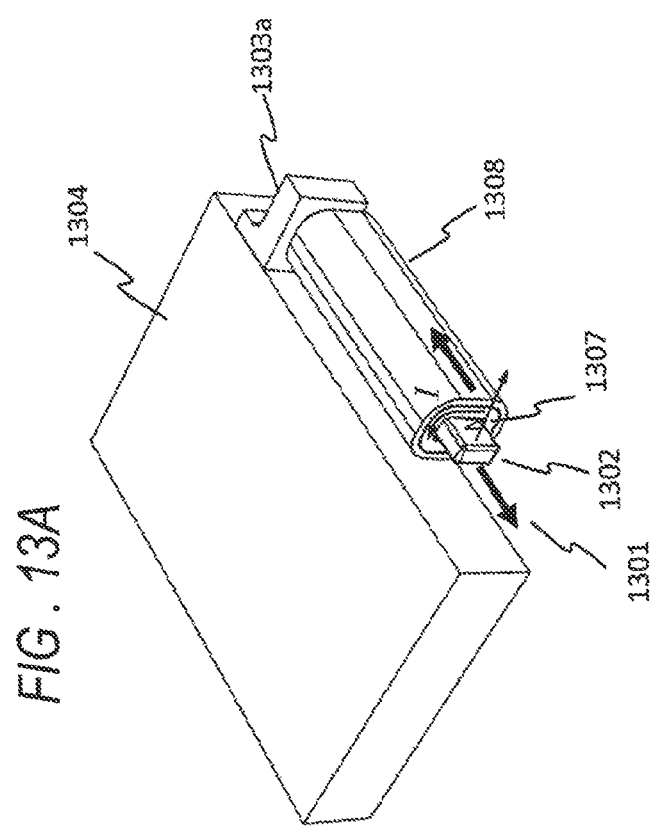

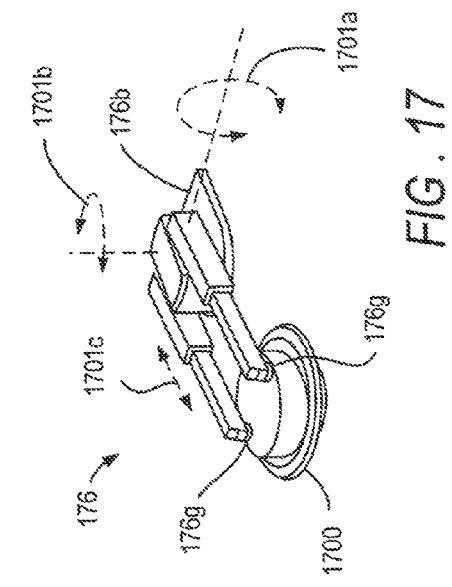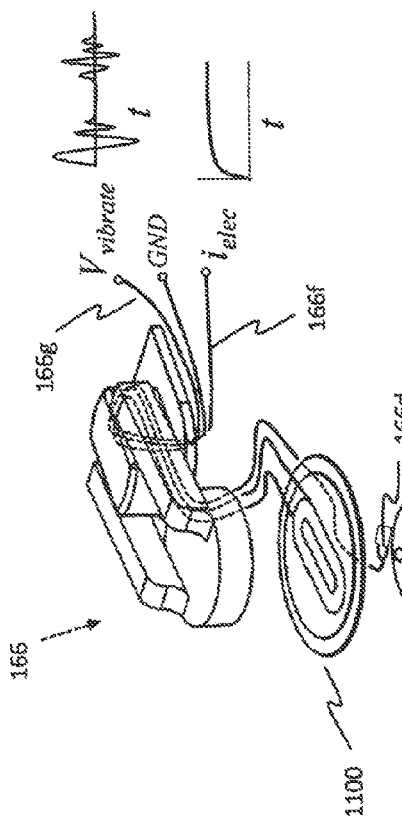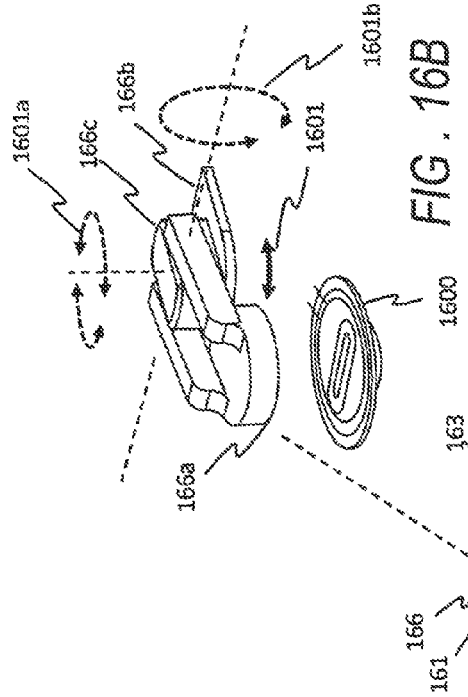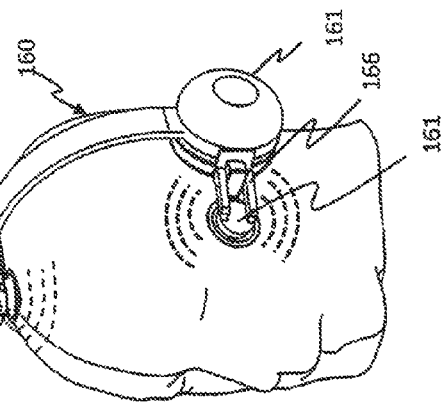
FIG. 16A
FIG. 16B
FIG. 16C
FIG. 17

SYSTEMS AND METHODS FOR GENERATING DAMPED ELECTROMAGNETICALLY ACTUATED PLANAR MOTION FOR AUDIO-FREQUENCY VIBRATIONS

CROSS-REFERENCE TO RELATED APPLICATIONS

This application claims the benefit of U.S. Provisional Patent Application Ser. No. 62/054,712, entitled "DAMPED ELECTROMAGNETICALLY ACTUATED PLANAR MOTION FOR AUDIO-FREQUENCY VIBRATIONS," filed Sep. 24, 2014, and U.S. Provisional Patent Application Ser. No. 62/101,985, entitled "SYSTEMS AND METHODS FOR PROVIDING DAMPED ELECTROMAGNETICALLY ACTUATED PLANAR MOTION FOR AUDIO-FREQUENCY VIBRATIONS," filed Jan. 10, 2015, each of which is incorporated by reference herein in its entirety.

FIELD OF THE INVENTION

The present invention relates to tactile transducers that produce bass frequency vibrations for perception by touch.

BACKGROUND OF THE INVENTION

Below about 200 Hz, the lower the frequency of sound, the more it is perceived not only by vibration of the ear drum but also by touch receptors in the skin. This sensation is familiar to anyone who has "felt the beat" of strong dance music in the chest, or through the seat of a chair, or has simply rested a hand on a piano. The natural stimulus is both auditory and tactile, and a true reproduction of it is possible only when mechanical vibration of the skin accompanies the acoustic waves transmitted through the air to the ear drum.

The prior art in audio-frequency tactile transducers primarily employ axial shakers. FIG. 1 shows an exploded view of a prior art headphone set 10 that includes axial shaker 100, including moving mass 114 suspended on spiral-cut spring 112, stator 116, and voice coil 118. The construction of such axial shakers mimics conventional audio drivers in which the light paper cone is replaced with a heavier mass, and a more robust suspension is provided, typically a spiral-cut metal spring.

A drawback of this construction is the production of unwanted acoustic noise. This occurs because the axial shaker is mounted in the headphone ear cup with the motion axis pointed at the opening of the ear canal. FIG. 2A shows a perspective view of prior art headphone set 20 that includes an axial shaker that vibrates along the z-axis and stimulates the skin by plunging the ear cup against the side of the user's head. Axial movement of the mass causes a countermovement of the entire ear cup itself, which is typically sealed over the pinna. Thus, the same force that stimulates the skin under the ear cup cushions unfortunately also plunges air into the listener's ear canal, overwhelming the output of the audio driver and generating the excess unwanted acoustic noise.

FIG. 2B shows a graph illustrating the excess apparent bass audio generated by the prior art headphones of FIG. 2A. In particular, FIG. 2B illustrates that the relatively flat acoustic frequency response of the headphones alone (traces labeled "off") is degraded when the inertial shaker is turned on to progressively stronger levels (traces labeled "on"). In this example, significant audio is added to the acoustic frequency response, causing an undesirable bump of 10-20 dB in the 50-100 Hz range. The result is a bass-heavy sound in which upper frequencies are underrepresented, and the user's perception is one of muffled, muddy sound.

The problem of uneven frequency response is typically made worse by a lack of mechanical damping. Leaving the system underdamped means that steady state signals near mechanical resonance achieve high amplitude, leading to a peaked response, and that the system rings after excitation is stopped, further degrading audio fidelity. Such a bump is evident in the frequency response of the prior art (FIG. 2B), where actuating the tactile transducer increases the acoustic output of the headphone 10 to 20 dB above the 90 dB Sound Pressure level that is indicated by the "0" reference line.

Another approach in the prior art, also problematic, is the use of un-damped eccentric rotating motors ("ERMs") and un-damped linear resonant actuators ("LRAs"). Small, un-damped ERMs are incompatible with high-fidelity audio for a few reasons. First, it generally takes about 20 milliseconds to "spin up" an ERM to a frequency that produces an acceleration large enough to be felt. By then an impulse signal (for example, the attack of a kick drum) will have passed. Second, in an ERM the acceleration, which can be likened to a "tactile volume," and frequency, which can be likened to a "tactile pitch" are linked and cannot be varied independently. This linkage is fundamentally incompatible with acoustic fidelity.

The main drawback of LRAs is the dependence on the "resonance," that the name suggests. The devices are designed for tactile alerts, not fidelity, and so they resonate at a single frequency and produce perceptible vibration at only that frequency. For example a typical LRA might produce up to 1.5 g of acceleration at 175±10 Hz, but less than 0.05 g outside this 20 Hz range. Such a high Q-factor renders this sort of device useless for high fidelity reproduction of low frequency tactile effects in the 15-120 Hz range. Despite these problems, LRAs have been contemplated for vertical mounting in the top cushion of a headphone bow.

In addition to the limited frequency range of LRAs there is a another problem with using LRAs as audio-frequency tactile transducers is that a transducer mounted vertically between the headphone bow and the top of the skull flexes the bow. At a fine scale, this flexion makes the bow flap like the wings of a bird, where an ear cup is situated at each wing tip. The inward-outward component of the flapping plunges the ear cups against the sides of the wearer's head, again producing undesirable audio that competes with and distorts the acoustic response of the audio drivers in the ear cups.

To avoid such unwanted audio, one approach is to construct a low-profile, vibrating module which moves a mass in-plane (i.e. in the x-y plane of FIG. 2A). This approach minimizes the surface area that is oriented to cause the problematic axially directed acoustic radiation. When mounted in an ear cup, such an in-plane vibrating module produces motion parallel with the surface of the side of the head. This movement effectively shears the skin, creating tactile sensation with little effect on the volume of air trapped between the ear cup and the ear drum. Acoustic noise is therefore minimized. Consider the difference between sliding a glass over a table top (planar motion of the present invention) and plunging a toilet (axial motion, as used in prior art). Although this in-plane approach has been contemplated, the dielectric elastomer actuators proposed for this purpose are expensive and complex devices that require high voltage electronics. Another drawback of this approach was that no provision was made for critically damping those transducers. Accordingly the tactile acceleration frequency response was underdamped, with a claimed Q-factor of 1.5 to 3.

In terms of electromagnetic actuation, a relatively thin, flat arrangement of a coil and two magnets that produces planar motion has been disclosed. In particular, the vibration module includes a single-phased electromagnetic actuator with a movable member comprised of two parallel thin magnets magnetized transversely in opposite directions and connected by a magnet bracket, and a means for guiding the magnet bracket.

Although this general approach to providing electromagnetic actuation has not been applied in headphones, it has been applied to the problem of providing haptic feedback in computer input devices like joysticks. One such device includes an actuator comprising a core member having a central projection, a coil wrapped around the central projection, a magnet positioned to provide a gap between the core member and the magnet, and a flexible member attached to the core member and the magnet. In this design, the motion is guided by a parallel pair of flexures.

A drawback of this guiding approach is the vulnerability of flexures to buckling when loaded by longitudinal compression. Compressive longitudinal loads on the flexures arise naturally from the attraction of the magnet pair riding the flexures to iron flux guides on the coil side, such as the E-core that provides the central projection supporting the coil. Accordingly, the flexures must be thick enough to resist this load without Euler buckling. This thickness comes at the expense of increased stiffness in the motion direction, which may undesirably impede movement.

Despite this drawback, the general approach has been applied elsewhere. For example, a flexure-guided surface carrying the magnets has been contemplated for use as the face of a massaging element. One approach to mitigating the buckling problem is to bear the compressive load on an elastic element such as foam. Supporting the load with an elastic element has some undesirable drawbacks, however. The foam adds stiffness in the direction of travel, and may significantly increase the thickness of the assembly, since the foam layer must be thick enough that the maximum shear strain (typically <100%) allows adequate travel.

An alternative approach to suspending a moving element arranges the long axis of the flexures in the plane of a substantially flat transducer. Because slender flexures resist transverse shear loads more effectively than longitudinal compressive loads, thinner flexures may be used, providing less impediment to motion.

Therefore, there exists a need for novel audio-frequency tactile transducers and devices.

SUMMARY OF THE DISCLOSURE

In some embodiments, proposed herein is a thin, flat vibration module with a movable member that is electromagnetically actuated to produce motion in-plane. Motion of the movable member can be damped so that the steady-state sinusoidal voltages applied to the module at different frequencies produce an acceleration response of the movable member that is substantially uniform over the range of 40-200 Hz. The module can be mounted in a headphone so that the motion axis lies substantially parallel to the sagittal plane of the wearer's head, so that the motion does not plunge the ear cup toward the wearer's ear canal, which produces unwanted audio and/or distortions.

In some embodiments, the module may consist of a mass and thin magnets, polarized through their thickness, where the mass and magnets are movably suspended inside a housing. The suspension may include flexures, bushings, ball bearings, or a ferrofluid layer, for example. The housing may include one or more conductive coils that carry electrical current used to vibrate the movable portion. To facilitate mounting of the module in the ear cup of a headphone, the geometry of the mass, coil, and housing may be substantially planar, (e.g. with a thickness less than one-third the length or width). The vibration of the moving portion may be damped using a suitable approach, such as the shearing of a layer of ferrofluid, oil, grease, gel, or foam, or the passage of air through an orifice, for example.

In some embodiments, flexures suspending the mass and magnets can be molded into the housing. In yet another embodiment, flexures may have tabs that engage receiving holes in the housing.

In some embodiments, the mass may have a central pocket that provides space for the magnets and coil. In other embodiments, the mass may lie adjacent to the magnets. In still other embodiments, the mass may be a battery for powering the module.

In some embodiments, the flexures can extend radially from a central hub to guide torsional rotation of the magnets and mass. Mounted in an ear cup in a plane parallel with the wearer's sagittal plane, these embodiments produce torsional rotation of the ear cup cushion against the wearer's skin. Multiple magnets and coils may be used in place of a single electromagnetic element.

In some embodiments, the module may be made of compliant materials suitable for direct skin contact. The skin-facing portion of the housing may be comprised of a stretchable cover. The magnets underneath this cover may be embedded in a puck comprised of compliant elastomer. The puck may be suspended on a layer of ferrofluid. The upper cover may be sealed at the perimeter to a lower cover to provide an impermeable compliant housing that holds the puck and ferrofluid in proximity to a coil. The underlying coil itself may be embedded in a compliant elastomeric material so that the entire module is compliant.

Planar motion of the module may be provided by various arrangements of magnets and coils. In some embodiments, a mass may be urged laterally by a magnet that is polarized along the axis of motion. To reduce the module's thickness, the lateral dimension of the magnet may be elongated, fitted with flux guides, and may be driven by an elongated oval coil that operates within an air gap defined by the flux guide. In other embodiments, the mass may be urged laterally by several magnets polarized along the motion axis, arranged side-by-side, and situated on the one edge of the mass. In still other embodiments, a long thin magnet polarized through the thickness direction may lie within a coil. Movement of the magnet within the coil may be coupled to the mass by brackets, and the motion of the magnet within the tube may be guided by ferrofluid bearing.

In some embodiments, the module can be provided with a clear plate that enables viewing of the motion within it. The module may be mounted in an ear cup with a window that provides a view of the motion inside the module. The ear cup may include a retaining element for the module.

In some embodiments, the complaint module may be integrated directly into cushions on the headphone bow, so as to apply vibratory shear tractions to the skin. In other embodiments, one or more of the modules may be mounted on movable armatures fixed to the ear cup and or bow of the headphones. The armatures may include rotational and prismatic degrees of freedom, and may be spring loaded to oppose the module to the skin, and may also be electromechanically actuated to produce a massaging motion on the skin of the scalp or face. The armature may include routing for electrical leads of the coil and/or an electrode that makes contact with the skin. The electrode may provide a means of recording electrical potential on the body surface, and/or for electrical stimulation of the wearer.

Still other objects and advantages of the present invention will in part be obvious and will in part be apparent from the specification.

The present invention accordingly comprises the features of construction, combination of elements, and arrangement of parts all as exemplified in the constructions herein set forth, and the scope of the invention will be indicated in the claims.

BRIEF DESCRIPTION OF THE DRAWINGS

For a fuller understanding of the inventive embodiments, reference is had to the following description taken in connection with the accompanying drawings in which:

FIG. 3A shows a chart illustrating two physical bounds on the force output of an electromagnetic vibration module arising from limitations on the space available for translating the mass and from the limited force output of the coil;

FIG. 3B shows a cross-sectional view of an exemplary module including an arrangement of a coil, magnets and a suspended inertial mass obeying the constraints illustrated in FIG. 3A, in accordance with some embodiments;

FIG. 3C shows a cross-sectional view of the module of FIG. 3B with exemplary magnetic flux lines superimposed thereon, in accordance with some embodiments;

FIG. 4A shows a perspective view of an exemplary damped planar electromagnetic module, in accordance with various embodiments described herein;

FIG. 4B shows an exploded view the module of FIG. 4A, in accordance with various embodiments described herein;

FIG. 6A shows an exploded view of an exemplary suspension, in accordance with various embodiments described herein;

FIG. 6B shows a detailed perspective view of a portion of the exemplary suspension of FIG. 6A, in accordance with various embodiments described herein;

FIG. 9A shows an exploded view of an exemplary compliant vibration module, in accordance with various embodiments described herein;

FIG. 9B shows a cross-sectional view of the compliant vibration module of FIG. 9A, in accordance with various embodiments described herein;

FIG. 10A shows an illustrative two-dimensional finite element analysis of a coil carrying a current in the magnetic gap formed by a single magnet and flux guides, in accordance with various embodiments described herein;

FIG. 10B shows a perspective view of an exemplary module having multiple cylindrical coils in circular magnetic gaps driving magnets coupled to an inertial mass, in accordance with various embodiments described herein;

FIG. 11 shows a perspective view of an exemplary elongated version of the coil and gap, driving an elongated magnet and mass, in accordance with various embodiments described herein;

FIG. 12 shows a cross-sectional view of an exemplary housing with elements to guide the lateral translation of the mass and magnets as they are driven by the coil(s) at one end, in accordance with various embodiments described herein;

FIG. 13A shows a perspective view of an exemplary vibration module, in accordance with various embodiments described herein;

FIG. 13B shows an exploded view of the module of FIG. 13A illustrating the suspension and attachment to the housing, in accordance with various embodiments described herein;

FIG. 16A shows a perspective view of a user wearing an exemplary headphone with armatures that position vibrating elements, in accordance with various embodiments described herein;

FIG. 16B shows an exploded view of the armatures of FIG. 16A illustrating degrees of freedom afforded by an example of an armature, in accordance with various embodiments described herein;

FIG. 16C shows an exploded view of an exemplary positioner with vibration element and electrode, in accordance with various embodiments described herein; and FIG. 17 shows a perspective view of another exemplary positioner, in accordance with various embodiments described herein.

DETAILED DESCRIPTION OF THE PREFERRED EMBODIMENTS

Figure 1:
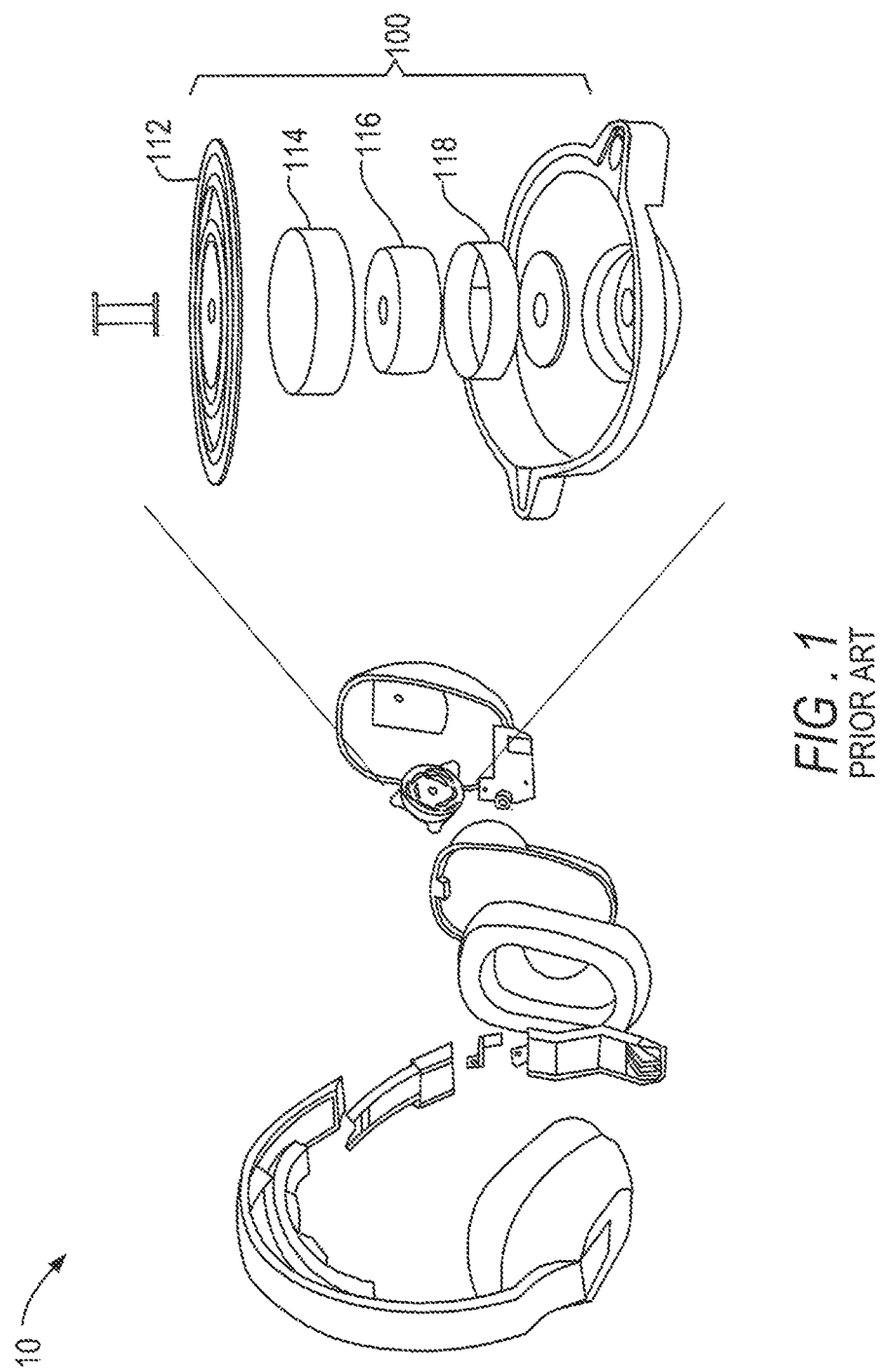
FIG. 1 shows an exploded view of a prior art headphone set having axial shaker suspended on a spiral-cut spring.
Figure 2B:
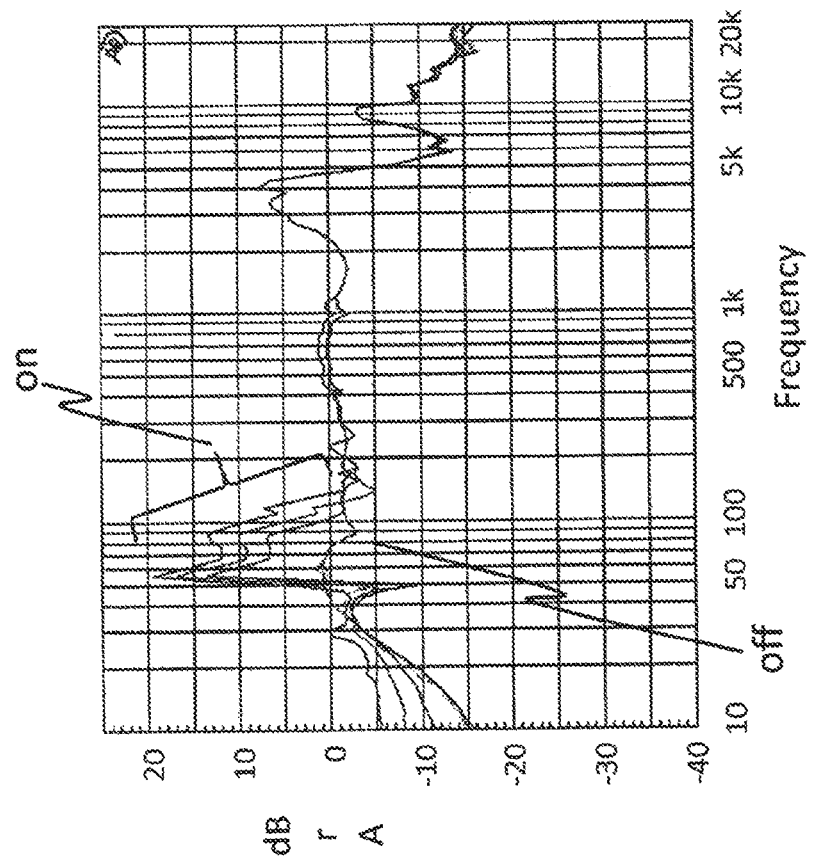
FIG. 2B shows a graph illustrating the excess bass audio apparent generated by the prior art headphones of FIG. 2A.
Figure 2A:
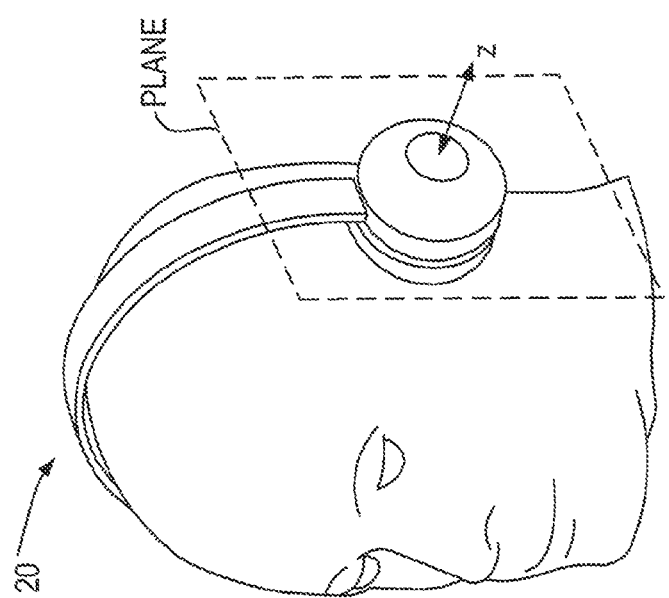
FIG. 2A shows a perspective view of a prior art headphone illustrating an axial shaker orientation that stimulates the skin by plunging the ear cup against the side of the head.

Various embodiments for providing damped electromagnetically actuated planar motion for audio-frequency vibrations are disclosed herein. The force output across a frequency range of a tactile transducer used for this purpose is limited by the space available for moving the internal mass and the peak force of the actuator causing the movement. FIG. 3A shows chart 30 illustrating these two physical bounds on the force output of an electromagnetic vibration module arising from limitations on the space available for translating the mass and from the limited force output of the coil. For an electromagnetic actuator, these limits may be termed travel limit 31 and coil limit 32, respectively. If the system is not underdamped, the output of the transducer can be described by a curve in region 33, below these limits 31 and 32.

The travel limit obeys the equation:

$$F_{max} = m x_{max} (2\pi f)^2 \qquad (1)$$

where:
$F_{max}$=[N], maximum force
$x_{max}$=[m], space in package available for displacement
m=[kg], mass in motion
f=[Hz], frequency FIG. 3B shows an exemplary vibration module 300 obeying the constraints illustrated in FIG. 3A, in accordance with some embodiments. In particular, FIG. 3B illustrates how travel limit 31 and coil limit 32 apply to embodiments of the present invention, which may generally include moving mass 304, oppositely polarized magnets 302a and 302b (collectively oppositely polarized magnets 302), coil 307, flux guides, 308, and housing 305.

In one particular example, travel limit 31 for vibration module 300 may be calculated for moving mass 304 having a mass of 0.015 kg that can undergo a maximum displacement of ±0.002 m ($x_{max}$) before contacting the wall of housing 305. In this example the product of mass and available displacement are (0.015 kg)·(0.002 m)=3E−5 kg·m. To maximize force, the product of mass and available travel should be maximized. The higher the frequency of interest, the greater the acceleration that is possible, up to some limit imposed by the actuator. For an electromagnetic actuator, this coil limit 32 typically reflects the maximum current I that can be put through the copper windings. There are also an instantaneous limit associated with the power supply and a longer term limit—typically seconds to minutes—associated with overheating the coil. In some embodiments, the mass times the displacement may be, for example, 1×10⁻⁵ kg-m or greater.

FIG. 3C illustrates the parameters that affect the coil limit. In particular, oppositely polarized magnets 302 produce a magnetic field B transecting coil 307 formed from a wire of length l. The Lorentz force F arising from the current transecting the magnetic field is:

$$F_{max} = i_{max} \int d\vec{l} \times \vec{B} \qquad (2)$$

where:
$F_{max}$=[N], maximum force
$i_{max}$=[Amp], current limit of supply, or thermal limit
l=[m], wire length
B=[Tesla], magnetic field strength Force output may be maximized by arranging coil 308, magnets 302, and flux guides 308 to steer maximum magnetic flux B through coil 307 cross-section carrying current I, and to provide a low-resistance path for heat out of the coil so that current $I_{max}$ does not produce an unacceptable temperature rise. For illustration, a practical coil limit of 1 N Force is assumed in FIG. 3A. Together the travel limit and coil limit define the maximum steady-state force output of a critically damped transducer.

FIGS. 4A and 4B show, respectively, a perspective and exploded view of an exemplary damped planar electromagnetic vibration module (vibration module 400), in accordance with various embodiments described herein. In some embodiments, vibration module 400 may be generally flat or planar so that it can easily be incorporated into the ear cup of a headphone, and provide a reciprocating force along axis 401 orthogonal to the thinnest dimension of the vibration module.

As shown in FIG. 4B, a pair of oppositely polarized magnets 402 can be held by a retainer 403 in a pocket or depression formed in mass 404, which may be suspended on flexures 406 within a frame or housing 405. Flexures 406 provide for movement of inertial mass 404 and magnets 402 along axis 401, which may be orthogonal to the thinnest dimension of the vibration module. Lateral forces can be imparted to magnets 402 by virtue of a Lorentz force generated by passing current through an coil 407, which is depicted in FIG. 4B as an elongated coil of conductive wire. Upper flux guide 408, which may be a piece of iron, or other suitable ferromagnetic material, adhered to or otherwise placed in close proximity to coil 407, can guide the magnetic flux and act as a heat sink and means of retaining coil 407 in place within housing 405. For example, magnetic flux guide 408 can retain coil 407 in slot 409 formed in top plate 405a of housing 405 so that coil 407 is fixed with respect to frame 405. In some embodiments, a portion of the housing (e.g. top plate 405a in the embodiment depicted in FIG. 4) supporting the coil (e.g. coil 407) can be a printed circuit board with components to provide low-pass filtering of an audio signal and/or power amplification for driving the coil.

In some embodiments, movement of the mass 404 and magnets 402 may be damped by thin layer of viscous ferrofluid 410 retained in a gap between the magnets 402 and bottom plate 405b of housing 405. An additional lower magnetic flux guide 408b may be provided to counterbalance the attractive force drawing magnets 402 toward upper flux guide 408a. Current may be routed to coil 407 using conductive leads 407a. In some embodiments conductive leads 407a may be soldered to solder pads 405aa formed on an accessible surface of housing 405 (e.g. a top surface of top plate 405a as shown in FIG. 4B or any other outer surface). Leads from a power source (not shown) may also be attached to solder pads 405aa in order to electrically couple the power source to coil 407.

Figure 5B:
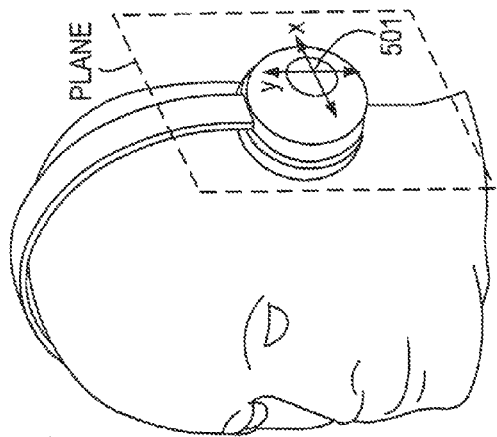
FIG. 5B shows a perspective view of a user wearing the headphone of FIG. 5A and illustrates how the motion axis lies parallel to the side of the user's head, in accordance with various embodiments described herein.
Figure 5C:
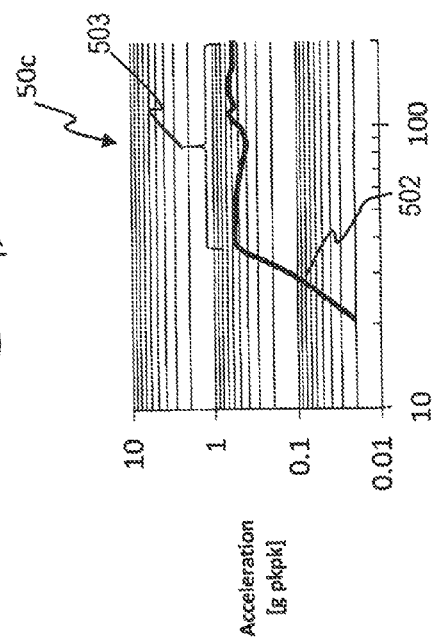
FIG. 5C shows that the measured acceleration of the exemplary headphone of FIG. 5A at various frequencies is approximately uniform over the range 40-200 Hz, in accordance with various embodiments described herein.
Figure 5A:
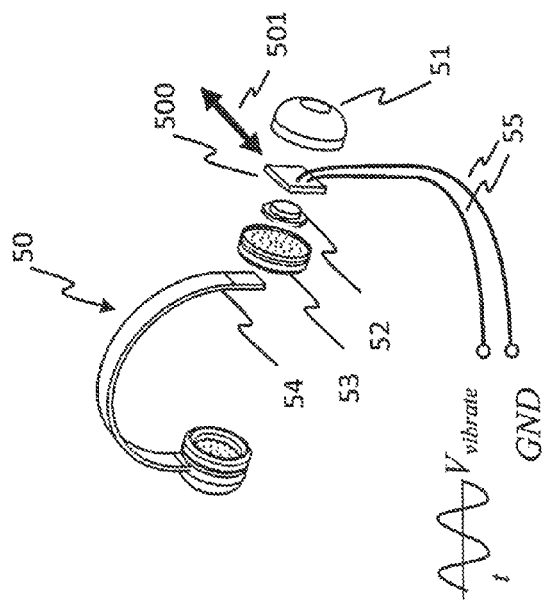
FIG. 5A shows an exploded view of an exemplary headphone showing the orientation of the module in the ear cup, in accordance with various embodiments described herein.

FIG. 5A shows an exploded view of exemplary headphone set 50 illustrating the orientation of vibration module 500 in the ear cup, in accordance with various embodiments described herein. Vibration module 500 is depicted mounted so as to occupy relatively little of the thickness of ear cup 51 and to provide a reciprocating force in an axis 501 substantially orthogonal to the thinnest dimension of the vibration module. Vibration module 500 can be situated behind audio driver 52 and sound baffle 53, which may be mounted on the headphone bow 54. Providing vibration modules that generate damped electromagnetically actuated planar motion for audio-frequency vibrations can advantageously speed a user's reaction time by adding tactile sensations to audio provided by the headphone set. The vibrations can also help to preserve the user's hearing by lowering the user's preferred acoustic listening level.

FIG. 5B shows a perspective view of a user wearing the headphone of FIG. 5A and illustrates how the motion axis lies parallel to the side of the user's head, in accordance with various embodiments described herein. As shown in FIG. 5B, a time-varying voltage can produce forces and accelerations in a plane parallel to the side of the headphone wearer's head along axis 501 labeled "x," though one skilled would appreciate that the forces and accelerations directed along a different axis, such as the axis labeled "y," for example, lying substantially in the same plane, may also be suitable for providing skin tractions that are perceptible as vibration while producing minimal excess sound.

FIG. 5C shows a chart 50c of experimental results of the measured acceleration of the exemplary headphone of FIG. 5A, in accordance with various embodiments described herein. In particular, chart 50c demonstrates that the measured acceleration of the ear cup along axis 501 is substantially uniform over the range 40-200 Hz. To characterize the frequency response, sinusoidal voltage ($V_{vibrate}$) ranging from 20 to 200 Hz was applied to one of the conductive leads 55 attached to the coil of vibration module 500 while the other lead was held at ground potential (GND) as shown in FIG. 5A.

Below approximately 40 Hz, in sub-resonance frequencies 502, the output of vibration module 500 is constrained by the "travel limit" (e.g. travel limit 31 of FIG. 3A) because as voltage is increased, the mass (e.g. mass 304 of FIG. 3B) travels farther, and increasing the voltage too high results in the travel exceeding $x_{max}$ and causes the mass to come into contact with the frame (e.g. housing 305 of FIG. 3B), producing an undesirable acoustic knocking sound. Above approximately 40 Hz, the system response is constrained by the "coil limit" (e.g. coil limit 32 of FIG. 3A) where increasing the voltage eventually produced an undesirable increase in coil temperature. The viscosity and volume of the damping fluid (e.g. viscous ferrofluid 410 of FIG. 4B) in vibration module 500 were adjusted to damp resonance that would be evident at 30-50 Hz, to achieve the relatively uniform, non-peaked, response evident in FIG. 5C between 40 and 200 Hz in range 503. The absence of resonant peak in the response makes it possible to reproduce the tactile component of a musical experience with previously unattainable high fidelity.

It will be evident to one skilled in the art that the embodiment of the vibration module presented in FIGS. 3A-4B is a particular, non-limiting example, meant merely to illustrate an exemplary vibration module that could be employed in accordance with various embodiments of the present invention. Additional exemplary vibration module embodiments will now be presented, each of which may be configured to produce appropriately oriented motion in a headphone as shown in FIGS. 5A-5C.

FIG. 6A shows an exploded view of vibration module 600, in accordance with various embodiments described herein. Vibration module 600 is substantially similar to vibration module 400, except that it is equipped with an alternative suspension system for accurately locating and spacing the suspended mass within the housing. In particular, vibration module 600 includes mass 604 to which flexures 606 are bonded on opposite ends, so as to suspend the mass within housing 605. Flexures 606 engage holes 605ab and 605bb in top plate 605a and bottom plate 605b, respectively. The pocket in the mass 604 may be equipped with bottom 608, embodied in FIG. 6A as a thin plate bonded to the mass. The magnet pair and portions of the housing are omitted in this instance for clarity.

FIG. 6B shows a detailed perspective view of a portion of flexure 606, in accordance with various embodiments described herein. Flexure 606 may include projecting tabs 606a that engage holes 605ab and 605bb in the top and bottom plates, to provide alignment of the plates and set the size of the gap between them. Flexures 606 may also have shoulders 606b that provide clearance for flexing member 606c to prevent contact between of the flexing member 606c and top plate 605a and bottom plate 605b as mass 604 travels within housing 605.

Figure 7:
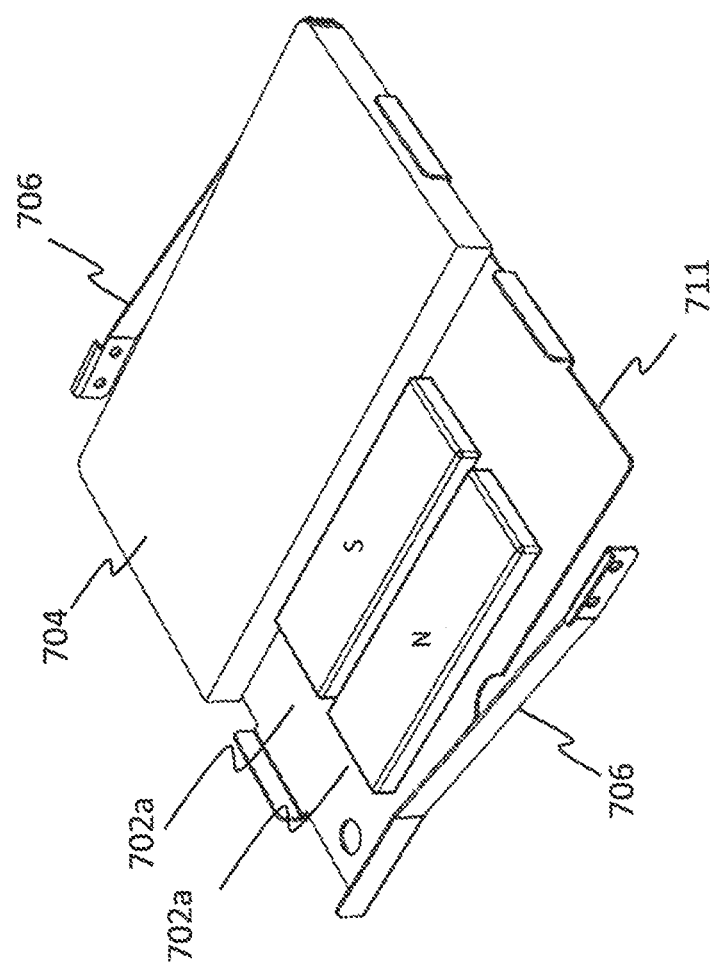
FIG. 7 shows a perspective view of a portion of an exemplary module, in accordance with various embodiments described herein.

FIG. 7 shows a perspective view of a portion of exemplary vibration module 700, in accordance with various embodiments described herein. Vibration module 700 includes oppositely polarized magnets 702 coupled to (e.g. affixed with an adhesive to) suspension base member 711. Flexures 706 may be formed integrally with or otherwise coupled to suspension base member 711. Mass 704 may be arranged and coupled to suspension base member 711 (e.g. at an end of the suspension base member 711 opposite magnets 702). In some embodiments, mass 704 may be or include a battery for powering vibration module 700. The portion of vibration module 700 depicted in FIG. 7 may be enclosed in a housing, not shown (e.g. housing 405 of FIG. 4).

Figure 8C:
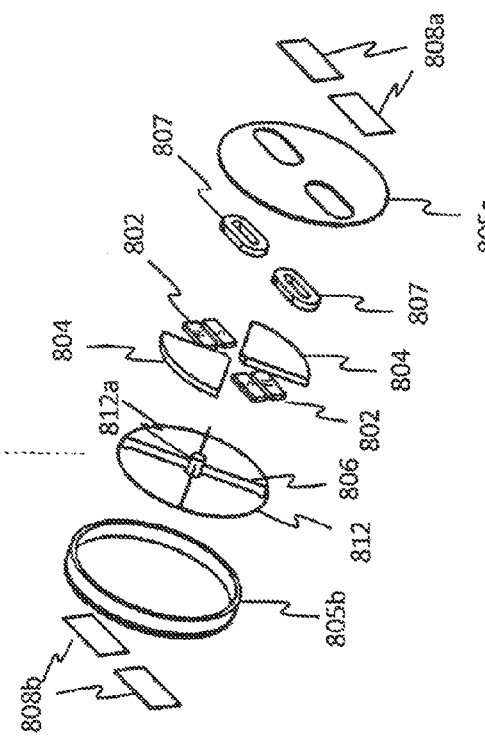
FIG. 8C shows a perspective view of a user wearing headphones incorporating the torsional module of FIG. 8A and illustrates exemplary rotational motion in a plane parallel to the side of the user's head, in accordance with various embodiments described herein.
Figure 8B:
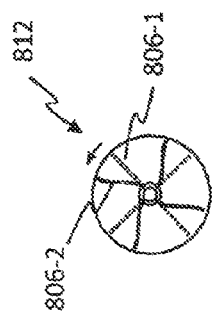
FIG. 8B shows a schematic view of the torsional module of FIG. 8A illustrating the action its flexures, in accordance with various embodiments described herein.
Figure 8A:
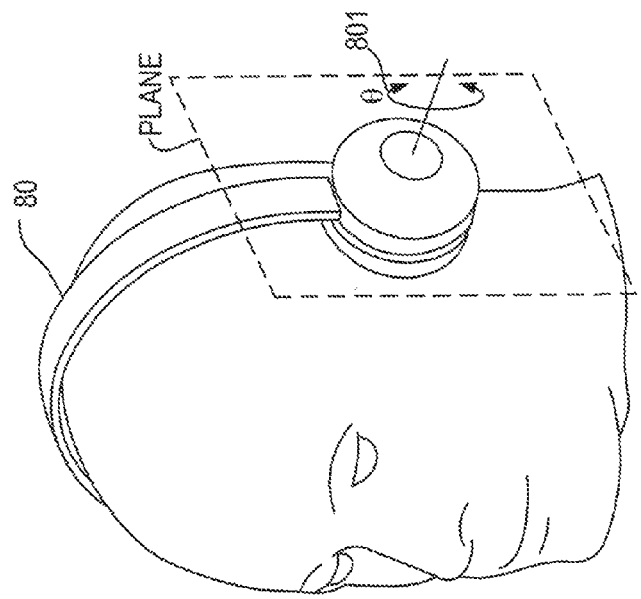
FIG. 8A shows an exploded view of an exemplary torsional module, in accordance with various embodiments described herein.

FIG. 8A shows an exploded view of exemplary torsional vibration module 800, in accordance with various embodiments described herein. Vibration module 800 is a rotational analog of the linearly traveling vibration module examples disclosed thus far. As shown in FIG. 8A two pairs of oppositely polarized magnets 802 and two inertial masses 804 may be coupled to a disk 812 suspended on flexures 806 that allow torsional rotation of the disk about central hub 812a. The ends of the hub may be coupled to front housing member 805a and back housing member 805b. Coils 807 can be retained in slots of front housing member 805a and either coupled to or brought into close proximity to magnetic flux guides 808a. Magnetic flux guides 808b may also be provided on back housing member 805b.

FIG. 8B shows a schematic view of torsional vibration module 800 illustrating the action of flexures 806, in accordance with various embodiments described herein. In particular, FIG. 8B illustrates the action of flexures 806 as they deflect from an initially straight position 806-1 to a deflected position 806-2 as disk 812 rotates about hub 812a.

FIG. 8C shows a perspective view of a user wearing headphone set 80 incorporating torsional vibration module 800 and illustrates exemplary rotational motion in a plane parallel to the side of the user's head, in accordance with various embodiments described herein. Rotation of the masses on central disk 812 produces counter rotation of the ear cup about the axis of the hub along rotational path 801 labeled "θ." The motion lies in the plane parallel to the side of the user's head, producing skin tractions perceptible as vibration, without causing a change to the volume of air inside the ear cup, thus minimizing unwanted sound. This particular embodiment of the rotational system has twice the number of coils and magnets of the linear systems illustrated previously, but produces the same general effect. Accordingly, one skilled in the art may appreciate that any number (N=1, 2, 3 . . . ) of actuator elements can provide equivalent or similar results. Likewise, it should be apparent to one skilled in the particular shape of the sectors housing masses 804 and magnets 802 may be varied, such that other shapes, such as half-circular sectors, can perform in an equivalent or similar manner to the explicitly disclosed embodiments.

Thus far, several rigid embodiments in accordance with the present invention have been disclosed. However, compliant constructions suitable for direct skin contact are also contemplated as falling within the scope of the invention. FIG. 9A shows an exploded view of exemplary compliant vibration module 900, in accordance with various embodiments described herein. Vibration module 900 can include a planar pair of oppositely polarized magnets 902 embedded in a compliant puck 904 supported on a layer of ferrofluid 911, where both puck 904 and ferrofluid 911 are trapped between two impermeable elastic membranes. The compliant materials used in formation of compliant vibration module 900 may have an elastic modulus of less than 50 MegaPascal.

Lower membrane 905b provides a stationary platform for movement, whereas the upper membrane 905a moves with the puck 904 and may optionally be corrugated to easily afford lateral movement of puck 904. The upper and lower membranes may be sealed at the circumference, for example by a heat sealing process for thermoplastic elastomers, by adhesive or solvent bonding, or any other suitable bonding method. As before, the magnets are urged laterally by current passed through coil 907. In this embodiment, the coil 907 can be enclosed in a compliant stage 905c so as to provide a supporting stage for movement of the puck 904.

Applying time-varying signals to lead 907a of coil 907 with respect to lead 907b produces time-varying forces on the puck 904, and corresponding lateral accelerations of upper membrane 905b coupled to it. Upper membrane 905b, in turn, may be placed in direct contact with the wearer's skin or may be integrated with the cushion fabric in contact with a wearer's skin.

FIG. 9B shows a cross-sectional view of compliant vibration module 900, in accordance with various embodiments described herein. As illustrated in FIG. 9B, current I flows through coil 907, urging magnets 902 laterally. Relative movement between the compliant upper membrane 905a and stage 905c is facilitated by the ferrofluid layer 911. The seal at the circumference of vibration module 900 is evident where the lower membrane 905b contacts upper membrane 905a.

Although examples so far have focused on vibration modules incorporating planar pairs of magnets, embodiments of the present invention are also contemplated having alternative arrangements between magnet and coil. Several exemplary embodiments are shown in FIGS. 10A-13.

FIG. 10A shows an illustrative two-dimensional finite element analysis of coil 1007 carrying a current in the magnetic gap formed by a single magnet 1002 and flux guides 1008, in accordance with various embodiments described herein. Magnet 1002 has magnetic flux that is guided by magnetic flux guides 1008 through an air gap in which coil 1007 carries current I. The generated Lorentz force urges coil 1007 in direction 1001a and the rest of the components illustrated in FIG. 10 in direction 1001b, opposing direction 1001a.

FIG. 10B shows a perspective view of exemplary vibration module 1000, in accordance with various embodiments described herein. Vibration module 100 can include multiple drivers including cylindrical coils in circular magnetic gaps driving magnets coupled to an inertial mass 1004. In some embodiments, one or more of these drivers may be situated along one edge of mass 1004, so that applying time varying voltage to coils 1007 generates Lorentz force on the magnets 1002 and flux guides 1008 and thereby urges mass 1004 to move along axis 1001 lying substantially in the plane of the vibration module. If coils 1007 are fixed to a housing (omitted for visual clarity) the magnets, flux guide, and inertial mass translate with respect to the housing.

FIG. 11 shows a perspective view of exemplary vibration module 1100 having a coil and gap structure that is integral and elongated with respect to the coil and gap structures of vibration module 1000, driving an elongated magnet 1102 and mass 1104, in accordance with various embodiments described herein. The resulting geometry uses an elongated oval coil 1107 arranged in the air gap of an elongated flux guide 1108. As with the previously disclosed embodiments, time-varying voltage sweeping current through coil 1107 urges the magnet, flux-guide, and inertial mass laterally along an axis 1101 in the plane of the module.

FIG. 12 shows a cross-sectional view of an exemplary housing 1205 with elements 1206 that guide the lateral translation of mass 1204 and magnets 1202 as they are driven by the coil(s) 1207 at one end, in accordance with various embodiments described herein. Housing 1205 may be a suitable housing for vibration modules 1000 and 1100 illustrated in FIGS. 10B and 11. Coil 1207 may be fixed to a wall of housing 1205. When current is passed through coil 1207, magnet 1202, flux guide 1208, and inertial mass 1204 are urged laterally along axis 1201 that lies in the plane of the vibration module. In this embodiment, the movement of inertial mass 1204 can, for example, be guided by linear glides 1206 rather than flexures. However, a person of skill in the art would recognize that a variety of suspensions lie within the scope of the present invention, and that comparable results may be achieved with flexures, a ferrofluid, bushings, and even ball bearings provided that they are pre-loaded and packed with viscous grease so as not to rattle audibly when reciprocated at frequencies in the 20-200 Hz range.

FIG. 13A shows a perspective view of yet another exemplary vibration module 1300, in accordance with various embodiments described herein. Vibration module 1300 includes thin magnet 1302 polarized along the thin axis. It operates in the center of a long coil with an oval cross section 1307. The flat sides of the oval carry current I running transverse to the flux of magnet 1302, and therefore generates a force perpendicular to both the current and the magnetic flux. That is, the Lorentz force urges magnet 1302 in a direction aligned with its long axis 1301, and urges coil 1307 in the opposite direction. Magnetic flux guide 1308 provided concentrically outside coil 1307 can improve orientation of the magnetic flux. Bracket 1303 can couple movement of magnet 1302 to inertial mass 1304.

FIG. 13B shows an exploded view of vibration module 1300 illustrating an exemplary suspension and attachment to housing 1305, in accordance with various embodiments described herein. Flexures 1306 can be attached to inertial mass 1304 so that inertial mass 1304 may move with respect to housing 1305. In some embodiments, housing may be provided with mating surface 1305a that may be coupled to magnetic flux guide 1308 provided around coil 1307 so that coil 1307 is fixed with respect to the housing. A second bracket 1303b for translating the motion of magnet 1302 to inertial mass 1304 is shown. Also shown is the axis of motion 1301 of inertial mass 1304.

Figure 14C:
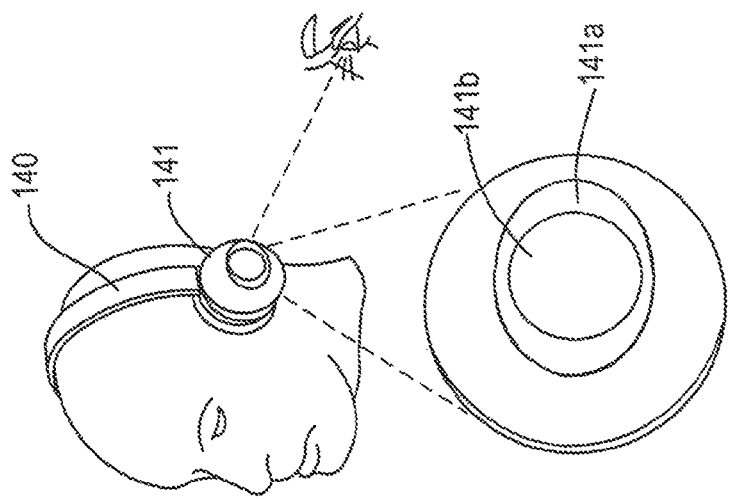
FIG. 14C shows a perspective view of a user wearing headphones including the headphone ear cup of FIG. 12A, in accordance with various embodiments described herein.
Figure 14B:
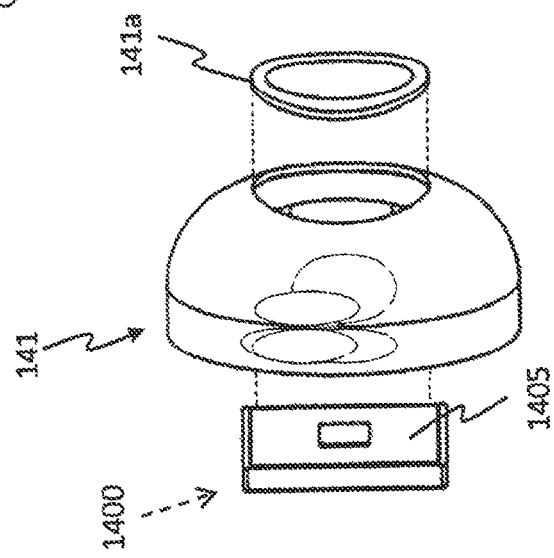
FIG. 14B shows an exploded view of the headphone ear cup of FIG. 12A, in accordance with various embodiments described herein.
Figure 14A:
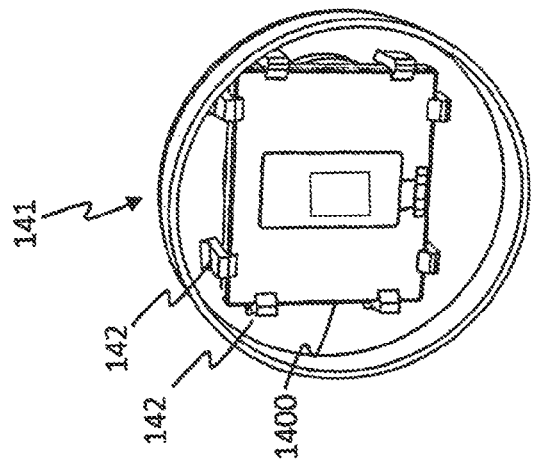
FIG. 14A shows a perspective view of an exemplary headphone ear cup with retaining features for a vibration module, in accordance with various embodiments described herein.

FIG. 14A shows a perspective view of an exemplary headphone ear cup 141 with retaining features 142 for holding a vibration module, in accordance with various embodiments described herein. Although clips are depicted in FIG. 14A, other suitable retaining features, such as adhesives and fasteners, for example, may be substituted.

FIG. 14B shows an exploded view of the headphone ear cup 141, in accordance with various embodiments described herein. In particular, FIG. 14B depicts an embodiments of the present invention in which movement of the inertial mass is visible through a wall of headphone ear cup 141. In this embodiment, the back plate 1405 of the vibration module 1400, is formed from a transparent material, such as glass or transparent plastic, for example, and headphone ear cup 141 is provided transparent window 141a. Together, back plate 1405 and transparent window 141a afford a view of the moving inertial mass 1404

FIG. 14C shows a perspective view of a user wearing headphone set 140, including headphone ear cup 141, in accordance with various embodiments described herein. As shown in FIG. 14C the edges of window 141a, on which a visual design 141b is optionally displayed, the movement of inertial mass 1404 and/or other components of vibration module 1400 are visible. That is, a viewer may be provided a clear optical path so that vibration of vibration module 1400 within ear cup 141 is visible when the vibration module is worn on a user's head.

Figure 15B:
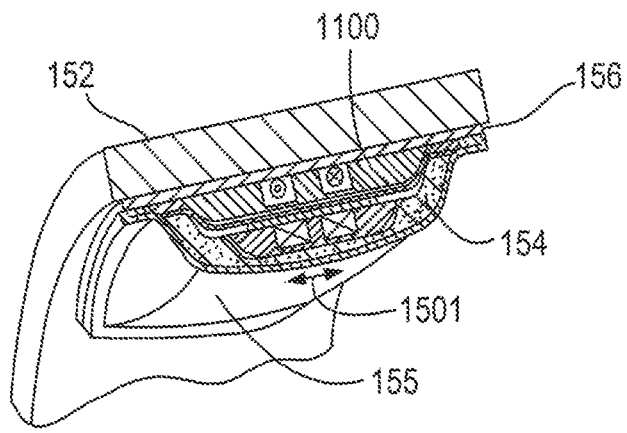
FIG. 15B shows a cut-away cross-sectional view of a portion of the headphone of FIG. 15A, in accordance with various embodiments described herein.
Figure 15A:
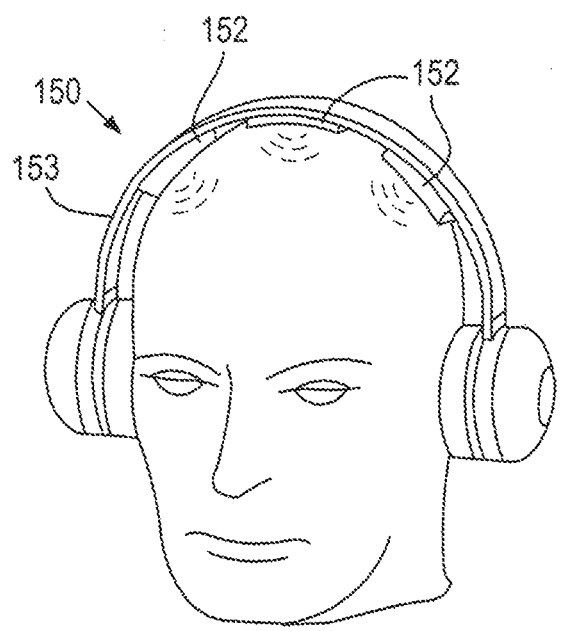
FIG. 15A shows a perspective view of a user wearing an exemplary headphone with multiple vibrating cushions situated on the headphone, in accordance with various embodiments described herein.

FIG. 15A shows a perspective view of a user wearing an exemplary headphone set 150 with multiple vibrating cushions 152, in accordance with various embodiments described herein. In particular, vibrating cushions 152 are provided on headphone bow 153 to produce tangential tractions on the wearer's skin at multiple locations.

FIG. 15B shows a cut-away cross-sectional view of a portion of headphone set 150, in accordance with various embodiments described herein. FIG. 15B illustrates headphone bow 153 and a compliant vibration module 1500, which may be similar to compliant vibration module 900 of FIGS. 9A and 9B, embedded in a cushion formed from foam member 154 and cover 155. The cushion may be attached (e.g. with adhesive 156) to headphone bow 153. In this embodiment, the movement of the compliant puck within vibration module 1500 causes shear movement 1501 of the cushion cover where it rests on the wearer's skin or hair.

FIG. 16A shows a perspective view of a user wearing an exemplary headphone set 160 with armatures 166 that position vibrating elements 162, in accordance with various embodiments described herein. As shown in FIG. 16A, one or more positioners 166 may be provided to adjust the locations of the vibrating elements 162 with respect to headphone bow 164 and ear cup 161, so as to provide vibrations at various locations on the wearer's skin.

FIG. 16B shows an exploded view of armatures 166 of FIG. 16A illustrating degrees of freedom afforded by an example of an armature, in accordance with various embodiments described herein. Here, a vibrating element, such as compliant vibration module 1600 (which may be similar or identical to compliant vibration module 900 of FIGS. 9A and 9B), is positioned so as to impose tangential shear tractions on the wearer's skin. The vibration axis may be chosen to lie primarily parallel to the user's sagittal plane (that is parallel with, but not necessarily coincident with the side of the user's head), to minimize unwanted movement toward and away from the user's ear, to minimize unwanted sound.

As further shown in FIG. 16B, armature 166 may provide a surface 166a that supports vibration module 1600 and also affords lateral movement 1601 over the surface of the user's skin, for example by rotation 1601a about a rotational degree of freedom provided by a pivoting base 166b. Armature 166 can also provide rotation 1601b about a second degree of freedom by virtue of a hinged connection 166c between armature 166 and armature base 166b that allows movement that accommodates the variable height of the user's skin with respect to the positioner base 16b where it connects to headphone 160.

FIG. 16C shows an exploded view of positioner 166, in accordance with various embodiments described herein. In particular, FIG. 16C illustrates how electrical leads for the vibrating element 1600 may be routed through it, and how it affords a mounting point and electrical connection 166d for an optional skin-contact electrode 166e. Electrode 166e may, through an independent electrical lead 166f source or sink current independent of any time-varying voltage applied to the lead 166g of the vibrating element.

The skin contact electrode thereby provides a means of stimulating the wearer, for example to provide transcranial direct current stimulation. Because vibration masks pain, the pain commonly associated with electrical stimulation through the skin can be avoided. The electrode can also provide a one or more sensors for recording electrical potentials on the surface of the wearer's body, for example signals arising from the wearer's electroencephalogram, indicating brain activity, or the electrooculogram, indicating eye orientation, or the wearer's electromyogram indicating contraction of the facial muscles, the conductivity of the user's skin, indicating sweating, or any other electrical potentials on the surface of the wearer's body.

FIG. 17 shows a perspective view of another exemplary positioner 176, in accordance with various embodiments described herein. Positioner 176 can have an extensional degree of freedom 1701 that affords radial positioning of the skin contact point with respect to the positioner base 176b. Additional flexibility is optionally imparted to the orientation of the skin contact point by elastic pillars 176g that join the support for the vibrating element to the positioner. It is clear to one skilled in the art that these various degrees of freedom in the positioner may be passive, spring loaded, or electromechanically actuated to provide a massaging motion by positioning a vibration module over a desired location on a user's body.

It should be understood that the aspects, features and advantages made apparent from the foregoing are efficiently attained and, since certain changes may be made in the disclosed inventive embodiments without departing from the spirit and scope of the invention, it is intended that all matter contained herein shall be interpreted as illustrative and not in a limiting sense.

It is also to be understood that the following claims are intended to cover all of the generic and specific features of the invention herein described, and all statements of the scope of the invention that, as a matter of language, might be said to fall there between.

What is claimed is:

1. A vibration module for generating damped electromagnetically actuated planar motion, the module comprising:
   at least one conductive coil;
   at least one magnet arranged in operative proximity to the coil;
   a moveable member coupled to one of the at least one conductive coil and the at least one magnet;
   a suspension that guides the moveable member with respect to the other one of the at least one conductive coil and the at least one magnet; and
   a damping member in structural communication with the moveable member, wherein the damping member flattens the acceleration response of the module to a Q-factor of less than 1.5, over the frequency range of 40-200 Hz in response to steady-state sinusoidal signals applied to the at least one coil.

2. The vibration module of claim 1, further comprising:
a housing encapsulating the at least one conductive coil, the at least one magnet, the moveable member, the suspension, and the damping member.

3. The vibration module of claim 2, wherein the suspension comprises a plurality of flexures, each flexure of the plurality of flexures coupled:
at a first end to the moveable member; and
at a second end to the housing.

4. The vibration module of claim 2, wherein the vibration module sustainably urges, at least ten times per second, the moveable member with mass, m, through a displacement, x, and wherein together the mass and displacement have a product that is at least $mx=1\times10^{-5}$ kg-m.

5. The module of claim 2, wherein the suspension comprises at least one of a bushing, a ball bearing, and a ferrofluid layer.

6. The module of claim 2, wherein the at least one coil is affixed to the housing, and wherein the at least one magnet is affixed to the moveable member.

7. The module of claim 2, wherein the housing comprises a thickness dimension having a first extent and a width dimension, substantially orthogonal to the thickness dimension, having a second extent, wherein the first extent is less than one-third of the second extent.

8. The module of claim 7, wherein the housing further comprises a length dimension, substantially orthogonal to the width dimension and the thickness dimension, having a third extent, wherein:
the first extent is less than one-third of the third extent;
the width dimension and the length dimension define a movement plane of the module; and
the suspension that guides the moveable member lies substantially in the movement plane.

9. The module of claim 2, wherein the housing comprises a thickness dimension having a first extent and a radial dimension substantially orthogonal to the thickness dimension, wherein the first extent is less than one-third a diameter of the radial dimension, and wherein the suspension guides the moveable member torsionally in a plane arranged substantially orthogonal to the thickness dimension.

10. The module of claim 2, wherein both the movable member and the housing are comprised of at least one compliant material with a Young's modulus of less than 50 MegaPascal.

11. The module of claim 1, wherein the at least one magnet comprises two oppositely polarized magnets.

12. The module of claim 1, further comprising:
at least one magnetic flux guide to guide magnetic flux from the at least one magnet toward the at least one coil, wherein the coil is affixed to a magnetic flux guide of the at least one magnetic flux guide.

13. The module of claim 1, wherein the damping member comprises at least one of a ferrofluid, a non-magnetic viscous liquid, a viscous gel, passage of air through an orifice, and a foam.

14. A system for imparting shear vibrations, the system comprising:
at least one vibration module, each module comprising:
at least one conductive coil;
at least one magnet arranged in operative proximity to the coil;
a moveable member coupled to one of the at least one conductive coil and the at least one magnet;
a suspension that guides the moveable member with respect to the other one of the at least one conductive coil and the at least one magnet; and
means for damping motion of the moveable member, wherein the means for damping motion of the moveable member flattens the acceleration response of the at least one vibration module to a Q-factor of less than 1.5, over the frequency range of 40-200 Hz in response to steady-state sinusoidal signals applied to the at least one coil; and
an apparatus for imparting vibratory motion of the at least one vibration module to a user's skin in a plane substantially parallel to a user's skin.

15. The system of claim 14, wherein the apparatus is a head set, comprising:
a headphone bow with ear cups at opposite ends, wherein the at least one vibration module is coupled to at least one of the headphone bow or ear cups, and wherein the module guides motion of the moveable member in a plane substantially parallel to the surface of the user's head.

16. The system of claim 14, wherein the apparatus is a head set, comprising:
a headphone bow with ear cups at opposite ends; and
a plurality of armatures, each armature extending from one of the headphone bow and an ear cup and arranging a vibration module such that its vibratory motion is in a plane substantially parallel to a user's skin.

17. The system of claim 14, wherein the apparatus arranges the at least one vibration module such that the suspension guides the moveable member in a plane substantially parallel to a sagittal plane of a wearer's body.

18. A method for speeding a user's spatial reaction time and preserving the user's hearing, the method comprising:
affixing at least one electromagnetic actuator to a head-mounted audio display;
driving said actuator to apply shear vibration to a portion of the user's skin in proportion to sub-200 Hz frequencies present in an acoustic signal played by the audio display; and
damping the motion of said actuator to achieve an acceleration response of said actuator to a Q-factor of less than 1.5.

19. A vibration module for generating damped electromagnetically actuated planar motion, the module comprising:
at least one conductive coil;
at least one magnet arranged in operative proximity to the coil;
a moveable member coupled to one of the at least one conductive coil and the at least one magnet;
a suspension that guides the moveable member with respect to the other one of the at least one conductive coil and the at least one magnet; and
a damping member in structural communication with the moveable member, wherein the vibration module sustainably urges, at least ten times per second, the moveable member with mass, m, through a displacement, x, and wherein together the mass and displacement have a product that is at least $mx=1\times10^{-5}$ kg-m.

20. The vibration module of claim 19, wherein the damping member flattens the acceleration response of the module to a Q-factor of less than 1.5, over the frequency range of 40-200 Hz in response to steady-state sinusoidal signals applied to the at least one coil.

21. The vibration module of claim 19, further comprising:
a housing encapsulating the at least one conductive coil, the at least one magnet, the moveable member, the suspension, and the damping member.

22. The vibration module of claim 21, wherein the suspension comprises a plurality of flexures, each flexure of the plurality of flexures coupled:
   at a first end to the moveable member; and
   at a second end to the housing.

23. The module of claim 21, wherein the suspension comprises at least one of a bushing, a ball bearing, and a ferrofluid layer.

24. The module of claim 21, wherein the at least one coil is affixed to the housing, and wherein the at least one magnet is affixed to the moveable member.

25. The module of claim 21, wherein the housing comprises a thickness dimension having a first extent and a width dimension, substantially orthogonal to the thickness dimension, having a second extent, wherein the first extent is less than one-third of the second extent.

26. The module of claim 25, wherein the housing further comprises a length dimension, substantially orthogonal to the width dimension and the thickness dimension, having a third extent, wherein:
   the first extent is less than one-third of the third extent;
   the width dimension and the length dimension define a movement plane of the module; and
   the suspension that guides the moveable member lies substantially in the movement plane.

27. The module of claim 21, wherein the housing comprises a thickness dimension having a first extent and a radial dimension substantially orthogonal to the thickness dimension, wherein the first extent is less than one-third a diameter of the radial dimension, and wherein the suspension guides the moveable member torsionally in a plane arranged substantially orthogonal to the thickness dimension.

28. The module of claim 19, wherein the at least one magnet comprises two oppositely polarized magnets.

29. The module of claim 19, further comprising:
   at least one magnetic flux guide to guide magnetic flux from the at least one magnet toward the at least one coil, wherein the coil is affixed to a magnetic flux guide of the at least one magnetic flux guide.

30. The module of claim 19, wherein the damping member comprises at least one of a ferrofluid, a non-magnetic viscous liquid, a viscous gel, passage of air through an orifice, and a foam.

31. The module of claim 19, further comprising a housing encapsulating the at least one conductive coil, the at least one magnet, the moveable member, the suspension, and the damping member, wherein both the movable member and the housing are comprised of at least one compliant material with a Young's modulus of less than 50 MegaPascal.

32. A vibration module for generating damped electromagnetically actuated planar motion, the module comprising:
   at least one conductive coil;
   at least one magnet arranged in operative proximity to the coil;
   a moveable member coupled to one of the at least one conductive coil and the at least one magnet;
   a suspension that guides the moveable member with respect to the other one of the at least one conductive coil and the at least one magnet;
   a damping member in structural communication with the moveable member; and
   a housing encapsulating the at least one conductive coil, the at least one magnet, the moveable member, the suspension, and the damping member, wherein both the movable member and the housing are comprised of at least one compliant material with a Young's modulus of less than 50 MegaPascal.

33. The vibration module of claim 32, wherein the damping member flattens the acceleration response of the module to a Q-factor of less than 1.5, over the frequency range of 40-200 Hz in response to steady-state sinusoidal signals applied to the at least one coil.

34. The vibration module of claim 32, wherein the suspension comprises a plurality of flexures, each flexure of the plurality of flexures coupled:
   at a first end to the moveable member; and
   at a second end to the housing.

35. The module of claim 32, wherein the suspension comprises at least one of a bushing, a ball bearing, and a ferrofluid layer.

36. The module of claim 32, wherein the at least one coil is affixed to the housing, and wherein the at least one magnet is affixed to the moveable member.

37. The module of claim 32, wherein the housing comprises a thickness dimension having a first extent and a width dimension, substantially orthogonal to the thickness dimension, having a second extent, wherein the first extent is less than one-third of the second extent.

38. The module of claim 37, wherein the housing further comprises a length dimension, substantially orthogonal to the width dimension and the thickness dimension, having a third extent, wherein:
   the first extent is less than one-third of the third extent;
   the width dimension and the length dimension define a movement plane of the module; and
   the suspension that guides the moveable member lies substantially in the movement plane.

39. The module of claim 32, wherein the housing comprises a thickness dimension having a first extent and a radial dimension substantially orthogonal to the thickness dimension, wherein the first extent is less than one-third a diameter of the radial dimension, and wherein the suspension guides the moveable member torsionally in a plane arranged substantially orthogonal to the thickness dimension.

40. The module of claim 32, wherein the at least one magnet comprises two oppositely polarized magnets.

41. The module of claim 32, further comprising:
   at least one magnetic flux guide to guide magnetic flux from the at least one magnet toward the at least one coil, wherein the coil is affixed to a magnetic flux guide of the at least one magnetic flux guide.

42. The module of claim 32, wherein the damping member comprises at least one of a ferrofluid, a non-magnetic viscous liquid, a viscous gel, passage of air through an orifice, and a foam.

* * * * *